(12) United States Patent
Kamp et al.

(10) Patent No.: US 10,001,043 B2
(45) Date of Patent: Jun. 19, 2018

(54) METHOD AND DEVICE FOR OPERATING EXHAUST GAS SENSORS

(71) Applicant: Robert Bosch GmbH, Stuttgart (DE)

(72) Inventors: Bernhard Kamp, Tamm (DE); Ariel Di Miro, Stuttgart (DE); Bastian Roetzler, Markgroeningen (DE); Joerg Frauhammer, Gemmrigheim (DE); Michael Bessen, Stuttgart (DE)

(73) Assignee: Robert Bosch GmbH, Stuttgart (DE)

( * ) Notice: Subject to any disclaimer, the term of this patent is extended or adjusted under 35 U.S.C. 154(b) by 61 days.

(21) Appl. No.: 15/105,410

(22) PCT Filed: Dec. 12, 2014

(86) PCT No.: PCT/EP2014/077588
§ 371 (c)(1),
(2) Date: Jun. 16, 2016

(87) PCT Pub. No.: WO2015/091273
PCT Pub. Date: Jun. 25, 2015

(65) Prior Publication Data
US 2016/0312681 A1      Oct. 27, 2016

(30) Foreign Application Priority Data
Dec. 17, 2013   (DE) .................. 10 2013 226 175

(51) Int. Cl.
*F01N 11/00* (2006.01)
*F01N 9/00* (2006.01)
(Continued)

(52) U.S. Cl.
CPC ............... *F01N 9/00* (2013.01); *F01N 11/00* (2013.01); *F02D 41/1446* (2013.01);
(Continued)

(58) Field of Classification Search
CPC ........ F01N 11/00; F01N 9/00; F02D 41/1446; F02D 41/1466; F02D 41/1494;
(Continued)

(56) References Cited

U.S. PATENT DOCUMENTS

| 5,590,521 A | 1/1997 | Schnaibel et al. |
| 5,616,835 A | 4/1997 | Schnaibel et al. |

(Continued)

FOREIGN PATENT DOCUMENTS

| DE | 10133384 | 1/2003 |
| DE | 102006010094 | 9/2007 |

(Continued)

OTHER PUBLICATIONS

International Search Report for Application No. PCT/EP2014/077588 dated Mar. 27, 2015 (English Translation, 2 pages).

*Primary Examiner* — Laert Dounis
*Assistant Examiner* — Matthew T Largi
(74) *Attorney, Agent, or Firm* — Michael Best & Friedrich LLP

(57) ABSTRACT

The invention relates to a method and a device, in particular a control and evaluation unit, for operating at least one exhaust gas sensor for monitoring the functionality of an emission control system in the exhaust tract of an internal combustion engine, wherein the exhaust gas sensor is operated at least intermittently at high temperatures and has a thermal shock sensitivity inherent to the design, and in which a heating phase can be implemented at least intermittently prior to a regeneration phase or prior to a measuring operation phase, wherein a clearly lower temperature is set in this heating phase in comparison to the regeneration temperature or the measuring operation temperature. According to the invention, the function for dew point recognition and re-release of a dew point end is adaptively (Continued)

implemented and influenced by at least one water detection criterion or at least one flood detection criterion. By this means, an improved dew point detection is achieved after driving through water, as a result of a significant reduction of tolerances and an earlier release of the dew point end for the exhaust gas sensor.

16 Claims, 1 Drawing Sheet

(51) Int. Cl.
*F02D 41/14* (2006.01)
*F02D 41/22* (2006.01)
*G01N 15/00* (2006.01)
*G01N 15/06* (2006.01)

(52) U.S. Cl.
CPC ..... *F02D 41/1466* (2013.01); *F02D 41/1494* (2013.01); *F02D 41/222* (2013.01); *G01N 15/0656* (2013.01); *F02D 2200/0802* (2013.01); *G01N 15/0606* (2013.01); *G01N 2015/0046* (2013.01); *Y02T 10/40* (2013.01)

(58) Field of Classification Search
CPC .......... F02D 41/222; F02D 2200/0802; G01N 15/0656; G01N 15/0606; G01N 2015/0046

See application file for complete search history.

(56) References Cited

U.S. PATENT DOCUMENTS

| | | | |
|---|---|---|---|
| 9,377,425 B2 | 6/2016 | Di Miro et al. | |
| 9,719,907 B2 * | 8/2017 | Motomura | ......... G01N 15/0656 |
| 2007/0000235 A1 * | 1/2007 | Ohsaki | .................. F01N 11/002 |
| | | | 60/274 |
| 2007/0113539 A1 * | 5/2007 | Nakano | .................... F01N 3/021 |
| | | | 60/276 |
| 2007/0271904 A1 * | 11/2007 | Shouda | ................... F01N 9/005 |
| | | | 60/284 |
| 2010/0300068 A1 * | 12/2010 | Enomoto | ............ F02D 41/1494 |
| | | | 60/273 |

FOREIGN PATENT DOCUMENTS

| | | | | |
|---|---|---|---|---|
| DE | 102009003091 | | 11/2010 | |
| DE | 102012008462 | | 10/2012 | |
| DE | 102012008462 | A1 * | 10/2012 | ............ F01N 11/002 |
| DE | 102013223429 | A1 | 5/2015 | |
| WO | 2009112947 | | 9/2009 | |

* cited by examiner

METHOD AND DEVICE FOR OPERATING EXHAUST GAS SENSORS

BACKGROUND OF THE INVENTION

The invention relates to a method and a device, in particular a control-and-evaluation unit, for operating at least one exhaust-gas sensor for monitoring the functionality of an exhaust emission control system in the exhaust train of an internal-combustion engine, wherein the exhaust-gas sensor is operated at high temperatures at least temporarily and, due to its type of construction, exhibits a sensitivity to thermal shock, and in which prior to a regeneration phase or prior to a measuring-mode phase a heating phase can be carried out at least temporarily, wherein in this heating phase a distinctly lower temperature is adjusted in comparison with the regeneration temperature or measuring-mode phase.

The invention further relates to a device, in particular a control-and-evaluation unit for operating exhaust-gas sensors and for implementing the method as claimed in the invention.

Exhaust-gas sensors—such as, for example, lambda probes, particle sensors, HC sensors or nitrogen-oxide sensors—as claimed in the state of the art are based on ceramic sensor elements that in operation are heated at least temporarily.

Particle sensors (PM) are employed nowadays, for example, for monitoring the particulate-matter (soot) emission of internal-combustion engines and for on-board diagnosis (OBD), for example for functional monitoring of particle filters, for example of a diesel particle filter (DPF). Such a resistive particle sensor is described in DE 101 33 384 A1. The particle sensor has been constructed from two intermeshing, comb-like electrodes (interdigital electrodes IDE) which have been covered at least partly by a trapping sleeve. If particles from a stream of gas are deposited on the particle sensor, this results in an evaluable change in the impedance of the particle sensor, from which the quantity of accreted particles—and consequently the quantity of particles entrained in the exhaust gas—can be inferred.

If the particle sensor is fully laden, the accreted particles are burnt in a regeneration phase with the aid of a heating element integrated within the particle sensor. For this purpose, the ceramic of the sensor element is heated to high temperatures, ordinarily to >600° C. As a rule, the heating element exhibits a temperature-measuring structure (meander) with which the temperature of the particle sensor can be monitored and the heating power during this regeneration phase can be regulated.

In this regeneration phase the sensor element reacts sensitively to great local changes of temperature or to a thermal shock such as may arise as a result of incident water or drops of water. A thermal shock of such a type can lead to cracks in the sensor element. Similar problems also arise in the case of the other aforementioned exhaust-gas sensors. Therefore a sensor regeneration is demanded by the engine control unit only when, as claimed in a heat-quantity calculation in the engine control unit, no more water can be present at the installation position of the sensor.

Furthermore, a loading with water must be prevented from occurring while the temperature of the sensor element of exhaust-gas sensors of such a type is greater than a certain threshold-value temperature, typically about 200° C. Therefore, particularly after a cold start, as long as condensate may still be located in the exhaust train of an internal-combustion engine, operation with heating at a temperature >200° C. of the exhaust-gas sensors takes place only after a certain time in which it may be assumed that, in this time, all the water has either evaporated or been discharged, in the form of droplets, from the exhaust train by virtue of surges of gas in automotive operation. This moment is typically designated as the dew-point end (DPE) and depends on many conditions, for which reason this moment has to be determined in the specific application for each type of vehicle. Operation of the exhaust-gas sensors at temperatures >200° C. is then permitted, so long as no condensation of water in the exhaust train occurs in the region of the installation point of the sensor as a consequence of cooling.

Particle sensors and also other heated exhaust-gas sensors utilize known dew-point detection functions in order to detect whether liquid water is present in the exhaust train (see, for example, document DE 43 00 530 C2 or DE 43 38 342 C2). With these functions it is determined, on the basis of the exceeding of a pipe-wall temperature threshold and on the basis of the exceeding of a threshold quantity of exhaust-gas heat, that no more liquid water can be present at the location of the sensor. The limiting quantity of heat is, in turn, dependent on the pipe-wall temperature that was present at the start of the driving cycle. The temperatures taken as a basis for this—such as the exhaust-gas temperature and the pipe-wall temperature—are model-based in the contemporary practical realization and are reproduced in an exhaust-gas-temperature model.

As a result of intense loading of the exhaust system with water from outside, for example during fording travel or in the course of launching a boat into water along a slip-ramp, flooding may occur, whereby water penetrates into the exhaust train, as a result of which an intense cooling of the exhaust system may occur. Depending on the configuration of the exhaust system, this cooling cannot be detected by the engine control unit but may result in an exposure to danger as a result of thermal shock to the sensor element of the exhaust-gas sensors. This case has not been covered hitherto in a dating of the dew-point end—that is to say, water remains in the exhaust train, even though the previous DPE-detection function cannot detect this on the basis of limiting quantities of heat and pipe-wall temperatures. If the sensor is regenerated while or after this state has arisen, the risk of a thermal shock is particularly high.

Furthermore, also during fording travel the exhaust pipe may be cooled in such a manner that a condensation of liquid water occurs. The sensor is then loaded with drops of liquid. The dew-point detection function is frequently based on model temperatures (see, for example, DE 10 2006 010 094 A1) which, in turn, are based on temperature measurements that were carried out using sensors which, however, have been arranged upstream of the particle sensor and the aforementioned exhaust-gas sensors. Since these temperature sensors remain unaffected by the fording state, such a fording state cannot be detected. If the particle sensor is regenerated, for example, damage to the sensor may occur as a result of thermal shock, even though a dew-point end was detected.

Furthermore, an increase may occur in the IDE current signal, which is caused by the conductivity of liquid water. This may be misinterpreted as soot loading of the sensor element.

In other, as yet unpublished, parallel applications by the applicant—inter alia, for example, the application having internal file reference R.351847(corresponding to DE 1020 13223429)—fording-detection criteria and also flood-detection criteria are furthermore described. Furthermore, in the likewise as yet unpublished application by the applicant having internal file reference R.347466 (corresponding U.S. Pat. No. 9,377,425) a utilization of a combination of criteria for enabling the heating of the exhaust-gas sensor is also described.

SUMMARY OF THE INVENTION

It is an object of this invention to make available an improved method for dew-point detection and also to adapt a re-enabling of the dew-point end to the situation of fording travel.

It is furthermore an object of the invention to make available an appropriate device for implementing the method, in particular a control-and-evaluation unit.

The object relating to the method is achieved in that the function of a dew-point detection and the re-enabling of a dew-point end are carried out adaptively and are influenced by at least one fording-detection criterion or at least one flood-detection criterion. By virtue of this adaptation, the dew-point detection can be improved in comparison with the state of the art, since environmental influences that cannot be predicted by modeling, such as those described in the introduction, can also be taken into account. This serves, on the one hand, for enhanced protection of the exhaust-gas sensors incorporated in the exhaust train of the internal-combustion engine, but, on the other hand, also for an earlier resumption, which is thereby possible, of the measuring tasks of the exhaust-gas sensors, or for an earlier implementation of a necessary regeneration phase.

A particularly advantageous variant of the method provides that temperature quantities of temperature-measuring instruments that have been incorporated within the exhaust-gas sensor or near the exhaust-gas sensor in the exhaust train of the internal-combustion engine are used for the purpose of detecting the dew point, and these temperature quantities are used at least temporarily as substitutional quantities for otherwise modeled temperatures in the course of the dew-point detection. The influence of model tolerances can be reduced by this. This also holds if there is no fording state. For instance, smaller lead-time compensations may be provided with the method, as a result of which an earlier enabling of the dew-point end tends to be possible. This, in turn, allows an earlier enabling of the monitoring and the control/regulation of exhaust-gas aftertreatment systems and of the engine control/regulation. In particular, the determination of the temperature directly in or on the exhaust-gas sensor offers advantages here in situations such as fording travel in comparison with a temperature quantity ascertained by modeling.

In a preferred variant of the method, initial values of the modeled temperatures in the course of the dew-point detection, which may correspond to cooling curves of parts of the exhaust-gas sensor, are replaced by measured temperatures. Hence, in particular, the environmental influences, particularly those in the case of fording travel, can be taken into account better in the course of the dew-point detection, since the temperature quantities determined by modeling may deviate distinctly from the real temperature conditions, and consequently misinterpretations may occur and, where appropriate, necessary times up until a dew-point end may be calculated incorrectly.

In this connection it may, in addition, have been stipulated that differing limiting quantities of heat are chosen for the purpose of ensuring a sufficient drying of the exhaust train and of the exhaust-gas sensors incorporated therein, depending on whether the function of dew-point detection is based on model temperature quantities or measured temperature quantities. In the case of model temperature quantities, larger reserves are preset as a rule, in order to take model tolerances into account.

Furthermore, in a preferred practical variant of the method it may have been stipulated that by way of decision criterion for utilizing a model temperature quantity or a measured temperature quantity a temperature comparison between the model temperature quantity and the measured temperature quantity is carried out after a minimum shutdown time of the internal-combustion engine, and the minimum value of the two temperature quantities is used at this moment as input quantity for the dew-point detection. By this, it is ensured that the more critical, i.e. lower, temperature in the given case is taken into consideration in the course of the dew-point detection, and consequently a sufficiently long drying-phase can be realized.

In this connection, a variant of the method provides that in the event of the minimum shutdown time being exceeded the measured temperature quantity is used, and in the event of the minimum shutdown time being fallen short of or attained the minimum value of the two temperature quantities is used.

A further variant of the method provides that for the purpose of re-enabling the dew-point end (DPE) after a detected fording state or flooding state a limiting quantity of heat, adapted to the situation, is preset. Hence additional introductions of water—for example, as a consequence of a more intense formation of condensation by virtue of the cooling of the exhaust train in the case of fording travel, or the penetration of water in the case of flooding—can be taken into account in the course of the re-enabling of the dew-point end.

If, as an advantageous variant of the method provides, in the case of a detected flooding a higher limiting quantity of heat is preset than in the case of detected fording travel, it can be ensured that a sufficiently good drying of the components in the exhaust train, particularly of the exhaust-gas sensors, can take place. Since, in the case of fording travel without flooding, besides the moisture introduced by the combustion and the induction air merely a more intense formation of condensation may occur but otherwise no additional water is introduced, the limiting quantity of heat can therefore be designed to be smaller in comparison with a detected flooding. Hence it can also be ensured that the DPE enabling can be undertaken earlier.

With regard to a simplification of this function, it may also have been stipulated that both in the case of a detected flooding or fording travel a merely increased limiting quantity of heat is preset in comparison with a standard application, i.e. a dew-point enabling without the possibility of detection of flooding or fording. In this case the starting-point is a "worst case" examination, without any further differentiation being made.

Furthermore, it may have been stipulated that after annulment of a detected fording state or flooding state the limiting temperature of the modeled or measured temperature quantity is increased at least temporarily for the dew-point enabling. This may be done in the simplest case by means of an offset.

The previously described functionality of the dew-point detection and of the enabling of the dew-point end can be applied particularly advantageously in the case of exhaust-gas sensors that have been designed as lambda probes, particle sensors, nitrogen-oxide sensors, sensors for determining a hydrocarbon content in the exhaust gas, and/or other exhaust-gas sensors based on a ceramic sensor element. During their normal measuring mode said sensors exhibit, on the one hand, high operating temperatures or are subjected at least temporarily to high temperatures (>600° C.), as is the case, in particular, for the purpose of regeneration in the case of particle sensors. On the other hand, these sensors possess increased sensitivity to thermal shock, which, particularly in the case of fording travel as a consequence of intensified cooling or even in the case of a flooding of the exhaust-gas sensor, may result in a malfunction, even in irreversible damage. In this connection it is of particular interest that this type of exhaust-gas sensors are sufficiently dried after fording travel accompanied by flooding. This can be ensured with the previously described functionality for adaptive dew-point detection and DPE enabling. In addition, for the purpose of implementing the method it is advantageous that use may be made of temperature-measuring instruments that have been incorporated within these exhaust-gas sensors or at least spatially near them, so that no additional expenditure arises for the specific application.

A particularly advantageous application of the method arises if, by way of modeled temperature quantity in the case of the particle sensor used as exhaust-gas sensor, a temperature model is used for a pipe-wall temperature, and the signal of a temperature sensor integrated within the sensor element of the particle sensor, of an NTC resistor incorporated in situ on the particle sensor, or of a heating resistor of a heating element integrated within the particle sensor, is used for the measured temperature quantity. In particular, particle sensors exhibit a high sensitivity to thermal shock. Here it is of particular interest that regeneration phases for eliminating soot are only started or enabled if it has been ensured that no residual water is present and/or the sensor has already dried sufficiently. This can be ensured, on the one hand, by the presetting of the limiting quantity of heat, depending on detected fording travel or flooding, and, on the other hand, by the inclusion of measured temperature quantities for the function of dew-point detection, as previously described. These temperature quantities can be determined in the case of the particle sensor, on the one hand, by a measuring meander in the particle sensor, or by evaluating a resistance of the integrated heating element. Ordinarily, these items of temperature information are already available in connection with the regulation of the heating power for the particle sensor.

The object relating to the device is achieved in that the function of dew-point detection and the re-enabling of a dew-point end can be carried out adaptively in the control-and-evaluation unit and can be influenced by at least one fording-detection criterion or at least one flood-detection criterion, the control-and-evaluation unit exhibiting equipment for implementing the previously described method with its variants. Ordinarily, this equipment is already available in control-and-evaluation units as claimed in the state of the art. It is advantageous in this connection that no change of hardware has to be made in respect of the particle sensor or in respect of the control-and-evaluation unit for the purpose of implementing the method. This additional functionality can be realized exclusively by a software supplement. In this case, the control-and-evaluation unit may be realized as a stand-alone unit which, for example, lies close to the sensor on the particle sensor, or as an integral constituent of a higher-ranking engine controller.

BRIEF DESCRIPTION OF THE DRAWINGS

The invention will be elucidated in more detail in the following on the basis of an embodiment represented in the figures. Shown are.

DETAILED DESCRIPTION

Figure 1:
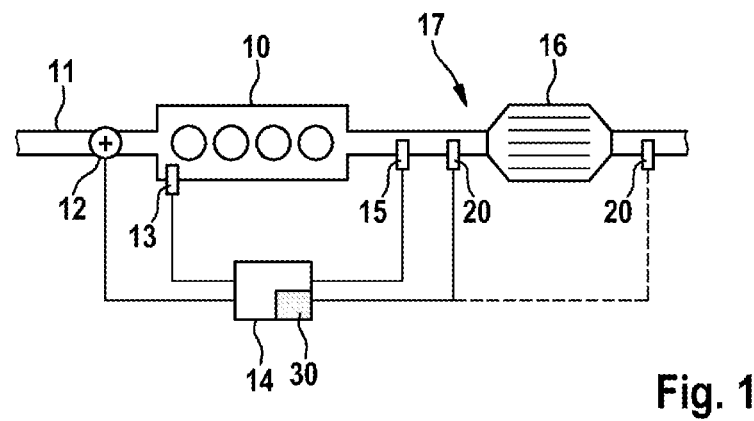
FIG. 1: in a schematic representation, the technical environment in which the method can be applied

FIG. 1 shows schematically the technical environment in which the method as claimed in the invention can be applied. An internal-combustion engine 10—which, for example, may have been realized as a diesel engine—receives combustion air supplied via an air feed 11. In this case the quantity of combustion air can be determined by means of a mass airflow meter 12 in the air feed 11. The quantity of air can be used in the course of a correction of a probability of accretion of particles that are present in the exhaust gas of the internal-combustion engine 10. The exhaust gas of the internal-combustion engine 10 is conducted away via an exhaust train 17 in which an exhaust emission control system 16 is arranged. This exhaust emission control system 16 may have been realized as a diesel particle filter. Furthermore, in the exhaust train 17 an exhaust-gas probe 15 realized as a lambda probe and a particle sensor 20 are arranged, the signals of which are supplied to an engine controller 14 or to a special control-and-evaluation unit 30 (sensor control unit SCU) which may be a constituent of the engine controller 14 or may have been realized as a stand-alone unit, for example close to the particle sensor 20. The engine controller 14 is furthermore connected to the mass airflow meter 12 and determines, on the basis of the data supplied to it, a quantity of fuel that can be supplied to the internal-combustion engine 10 via a fuel meter 13.

The particle sensor 20 may in this case also have been arranged downstream of the exhaust emission control system 16 in the direction of flow of the exhaust gas, which affords advantages with regard to a homogenization of the flow of exhaust gas at this point and is the case, in particular, when employed within the scope of on-board diagnosis. With the devices shown, an observation of the particulate emission of the internal-combustion engine 10 and a prognosis of the loading of the exhaust emission control system 16 taking the form of a diesel particle filter (DPF) is possible.

Figure 2:
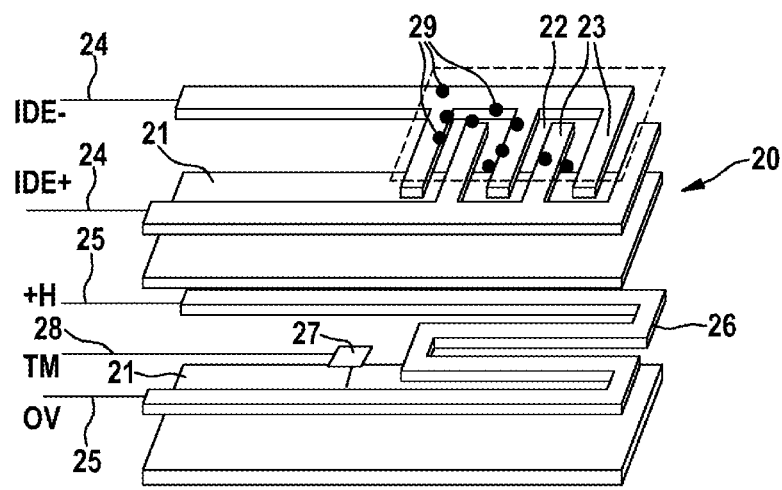
FIG. 2: schematically, a particle sensor in an exploded representation.

FIG. 2 shows, in a schematic representation, a particle sensor 20 corresponding to the state of the art, in an exploded representation.

On insulating substrates 21 consisting of ceramics, for example consisting of aluminum oxide, an IDE measuring structure 22 in the form of a first electrode and a second electrode has been applied. The electrodes have been realized in the form of two interdigital intermeshing comb electrodes and are designated as IDE electrodes 23 and constitute the actual sensor element. At the front ends of the IDE electrodes 23 the IDE terminals 24 (IDE+ and IDE−) have been provided, via which the IDE electrodes 23 for supplying voltage and for performing the measurement have been connected to the control-and-evaluation unit 30 (not represented in FIG. 2). In addition, in the example shown, a heating element 26 has been integrated between the insulating substrates 21, which has been connected to the control-and-evaluation unit 30 via additional heating-element terminals 25 (+H, OV).

For measuring the temperature, a temperature sensor 27 may additionally have been provided in the layered structure of the particle sensor 20, in which case a temperature-sensor terminal 28 (TM) has additionally been guided out of the particle sensor 20. By way of temperature sensor 27, resistive structures consisting of platinum—for example, the meander structure shown—may, for example, find application. Alternatively, at least a part of the structure of the heating element 26 may also be utilized as temperature sensor 27.

If such a particle sensor 20 is operated in a stream of gas conducting soot particles 29 —for example, in an exhaust-gas duct of a diesel engine or of a furnace installation—soot particles 29 from the stream of gas are deposited on the particle sensor 20. These particles possess a certain electrical conductivity. In this connection, besides depending on the particle concentration in the exhaust gas, the rate of deposition of the soot particles 29 onto the particle sensor 20 also depends, inter alia, on the voltage that is applied to the IDE electrodes 23. By virtue of the applied voltage, an electric field is generated which exerts a corresponding attraction on electrically charged soot particles 29. By suitable choice of the voltage applied to the IDE electrodes 23, the rate of deposition of the soot particles 29 can therefore be influenced.

In the embodiment, the IDE electrodes 23 and the uppermost insulating substrate 21, on which the IDE electrodes 23 are located, have been covered with a protective layer. This optional protective layer protects the IDE electrodes 23 against corrosion at the generally prevailing high operating temperatures of the particle sensor 20. In the present embodiment, said protective layer has been produced from a material having low conductivity, but it may also have been manufactured from an insulator.

Soot particles 29 from the stream of gas have been deposited in the form of a layer on the protective layer. By virtue of the slightly conductive protective layer, the soot particles 29 form a conductive path between the IDE electrodes 23, so that, depending on the quantity of the deposited soot particles 29, a change of resistance between the IDE electrodes 23 results. This change can be measured, for example by a constant voltage being applied to the IDE terminals 24 of the IDE electrodes 23 and by the change in the current through the accreted soot particles 29 being determined. If the protective layer has been constructed to be insulating, the deposited soot particles 29 result in a change in the impedance of the particle sensor 20, which can be evaluated by an appropriate measurement, preferably with an AC voltage.

If the particle sensor 20 has been covered with a layer of soot particles 29 to such an extent that additionally accreted soot particles 29 do not result in an additional change in the resistance or impedance of the particle sensor 20, the particle sensor 20 is regenerated within a regeneration phase. For this purpose, the particle sensor 20 is heated with the aid of the heating element 26 to such an extent that the adjacent soot particles 29 burn. This ordinarily happens at temperatures >600° C.

Prior to a regeneration of the particle sensor 20, for a certain time a protective heating ahead of the dew-point end (DPE) is carried out, as described in the introduction.

The method as claimed in the invention provides, on the one hand, that, in comparison with a standard application of a dew-point detection, a temperature measured by a temperature-measuring instrument on the exhaust-gas sensor, in the following example on the particle sensor 20, is utilized as input quantity for the dew-point detection, wherein the measured temperature is used as substitutional quantity for the pipe-wall temperature modeled hitherto. Hitherto it has been stipulated that an exhaust-gas-temperature model is initialized with starting values for exhaust-gas temperature and pipe-wall temperature. In this case, as claimed in the contemporary state of the art, use is made of a cooling curve of the pipe-wall temperature. This curve calculates the pipe-wall temperature at the end of the shutdown time of the internal-combustion engine 10 from the temperature values immediately prior to the shutdown time and from the duration of the shutdown time on the assumption of an exponential dependence on time. However, as mentioned in the introduction, this model cannot take environmental influences into account at all, or can only take them into account inadequately. Therefore it may have been stipulated that the initial values for pipe-wall temperatures from cooling curves are replaced by measured temperature values.

Furthermore, the pipe-wall temperature modeled hitherto enters into the calculation of a limiting quantity of heat. This may also use the temperature of the measuring instrument of the particle sensor 20. In this connection it may be appropriate to switch between alternative limiting quantities of heat. In this case, a set of limiting quantities of heat is utilized if measured temperatures on the basis of the temperature-measuring instrument are being utilized. A second set is utilized when model temperatures are being employed. In this connection, larger reserves can be allowed for, as a rule, in order to take model tolerances into account.

As decision criterion for the utilization of the temperature-measuring instrument instead of the model values, a variety of approaches may be pursued. After a minimum shutdown time of the internal-combustion engine 10 has been attained, it may be assumed that the temperature of the sensor element has been assimilated to the pipe-wall temperature. The temperature can consequently be influenced not only by a large temperature difference between gas temperature and pipe-wall temperature, by a past sensor regeneration or by a protective-heating state. Furthermore, it may have been stipulated that a minimum value is derived from the temperature of the measuring instrument of the particle sensor 20 and the model temperature. An appropriate combination of the two aforementioned values may also be used. In the event of a minimum shutdown time being exceeded, the temperature of the temperature-measuring instrument is regarded as valid in every case. In the case where the minimum shutdown time is fallen short of or is just attained, the minimum value of the two temperatures is selected.

As temperature-measuring instrument may be resistance-measuring elements, for example the resistive meander of the particle sensor 20 described in FIG. 2, which ordinarily exhibits a PTC characteristic, or an NTC measuring resistor incorporated in situ, or a heating resistor of the heating element 26 of the particle sensor 20.

With regard to a re-enabling of the dew-point end or a withdrawal of a dew-point detection of an exhaust-gas sensor after a fording state, it has furthermore been stipulated that the re-enabling of the dew-point end or the withdrawal of the dew-point detection is adapted to the situation of fording travel.

In the fording state, the exhaust-gas sensor is acted upon by water that has penetrated into the exhaust train or by water that has condensed as a consequence of external cooling of the exhaust train, and must not be regenerated without prior drying. If it is detected by a functionality that a fording state has arisen, a dew-point undershoot is detected and a sensor regeneration or a particle measurement at the particle sensor 20 is prevented. In this case, conditions adapted to the "fording state" situation apply to the re-enabling of the dew-point end.

For the purpose of enabling, a limiting quantity of heat adapted to the fording situation is preset which has to be conducted past the sensor together with the exhaust gas, so that said sensor is considered to have been dried. In this case it is possible to differentiate between a flooding of the exhaust system and fording travel—that is to say, transit through water without flooding of the exhaust train. In the case of a flooding of the exhaust train, this limiting quantity of heat is chosen to be higher than in the case of condensation by external cooling as a consequence of fording travel without flooding, since, in the first case, by virtue of the quantity of water introduced a greater quantity of heat is required for an enabling of the dew-point end in order to dry the components in the exhaust train than would be necessary without flooding of the exhaust train. In the case of fording travel without flooding, besides the water stemming from the combustion or from the induction air no additional water is introduced. Therefore the requisite limiting quantity of heat is smaller in this case.

In a simplified function of the re-enabling of the dew-point end or of the withdrawal of the dew-point detection, this differentiation can also be dispensed with. In this case, the starting-point is a "worst case" examination, wherein a larger limiting quantity of heat is chosen in comparison with a standard application as claimed in the state of the art.

If a detected fording state is annulled, it may furthermore have been stipulated that the limiting temperature for the re-enabling of the dew-point end is increased via the pipe-wall temperature, in order to take account of the fact that the existing functionality comes from excessive pipe-wall temperatures. In the simplest case this can be done by an applicable offset in the pipe-wall temperature.

The previously described functionality has preferably been implemented as a software module in an in-situ control unit of the particle sensor 20—that is to say, in a control-and-evaluation unit 30 of the particle sensor 20. But it may also be an integral constituent of the higher-ranking engine controller 14 (cf. FIG. 1).

In principle, the described functionality may also be applied to other exhaust-gas sensors in which a correct dew-point detection is likewise important for the functionality of the exhaust-gas sensors and as protection against damage as a consequence of thermal shock. Besides the previously described particle sensors 20, exhaust-gas sensors of such a type may also be, for example, lambda probes, HC sensors for measuring hydrocarbon concentrations, or nitrogen-oxide sensors, which, as claimed in the state of the art, are based on ceramic sensor elements that in operation are heated at least temporarily.

The invention claimed is:

1. A method for operating at least one exhaust-gas sensor for monitoring functionality of an exhaust emission control system in an exhaust train of an internal-combustion engine (10), including:
   operating the at least one exhaust-gas sensor at high temperatures at least temporarily and, due to its type of construction, the at least one exhaust-gas sensor exhibits a sensitivity to thermal shock,
   carrying out a heating phase at least temporarily prior to a regeneration phase or prior to a measuring-mode phase, wherein in the heating phase a distinctly lower temperature is adjusted in comparison with a regeneration temperature or a temperature in the measuring-mode phase, and
   adaptively carrying out a dew-point detection and re-enabling of a dew-point end that is influenced by a fording detection criterion when a fording state is determined and by a flood-detection criterion when a flooding state is determined.

2. The method as claimed in claim 1, wherein the dew-point detection includes using temperature quantities of temperature-measuring instruments incorporated within the at least one exhaust-gas sensor or near the at least one exhaust-gas sensor in the exhaust train of the internal-combustion engine (10), and these temperature quantities are used at least temporarily as substitutional quantities for otherwise modeled temperatures in the course of the dew-point detection.

3. The method as claimed in claim 1, wherein initial values of modeled temperatures in the course of the dew-point detection, which correspond to cooling curves of parts of the at least one exhaust-gas sensor, are replaced by measured temperatures.

4. The method as claimed in claim 1, wherein differing limiting quantities of heat are chosen for ensuring a sufficient drying of the exhaust train and of the at least one exhaust-gas sensor incorporated therein, depending on whether a function of the dew-point detection is based on model temperature quantities or measured temperature quantities.

5. The method as claimed in claim 1, wherein by way of decision criterion for utilizing a model temperature quantity or a measured temperature quantity, carrying out a temperature comparison between the model temperature quantity and the measured temperature quantity after a minimum shutdown time of the internal-combustion engine (10), and a minimum value of the model temperature quantity and a minimum value of the measured temperature quantity at this moment are used as input variables for the dew-point detection.

6. The method as claimed in claim 1, wherein in the event of a minimum shutdown time of the internal combustion engine being exceeded a measured temperature quantity is used, and in the event of the minimum shutdown time being fallen short of or attained a minimum value of a model temperature quantity and a minimum value of a measured temperature quantity are used.

7. The method as claimed in claim 1, wherein for re-enabling the dew-point end after the detected fording state or the detected flooding state, a limiting quantity of heat adapted to the detected fording state or the detected flooding state is preset.

8. The method as claimed in claim 7, wherein in the case of the detected flooding state a higher limiting quantity of heat is preset than in the case of the detected fording state.

9. The method as claimed in claim 7, wherein both in the case of the detected flooding state or the detected fording state, an increased limiting quantity of heat is preset in comparison with a dew-point enabling without the possibility of detection of flooding or fording.

10. The method as claimed in claim 1, wherein after annulment of the detected fording state or the detected flooding state, a limiting temperature of a modeled or a measured temperature quantity for the dew-point enabling is increased at least temporarily.

11. The method as claimed in claim 1, the at least one exhaust-gas sensor is from the group consisting of: lambda probes, particle sensors (20), nitrogen-oxide sensors, sensors for determining a hydrocarbon content in the exhaust gas, and other exhaust-gas sensors based on a ceramic sensor element, and temperature-measuring instruments are in the at least one exhaust-gas sensor or incorporated spatially near the at least one exhaust-gas sensor.

12. The method as claimed in claim 11, wherein by way of modeled temperature quantity in the case of the particle sensor (20) used as the at least one exhaust-gas sensor, a temperature model is used for a pipe-wall temperature, and a signal of a temperature sensor (27) integrated within the sensor element of the particle sensor (20), of an NTC resistor incorporated in situ on the particle sensor (20), or of a heating resistor of a heating element (26) integrated within the particle sensor (20), is used for a measured temperature quantity.

13. A device for operating at least one exhaust-gas sensor for monitoring functionality of an exhaust emission control system in an exhaust train of an internal-combustion engine (10), wherein the at least one exhaust-gas sensor is configured to operate at high temperatures at least temporarily by a control-and-evaluation unit (30) and, due to its type of construction, exhibits a sensitivity to thermal shock, and at least temporarily, prior to a regeneration phase or prior to a measuring-mode phase, the at least one exhaust-gas sensor exhibits a heating phase with a distinctly lower temperature in comparison with a regeneration temperature or measuring-mode phase, wherein dew-point detection and re-enabling of a dew-point end is carried out adaptively and influenced by one of the fording-detection criterion and the flood-detection criterion, wherein the control-and-evaluation unit (30) is configured to implement the method as claimed in claim 1.

14. A method for operating at least one exhaust-gas sensor for monitoring functionality of an exhaust emission control system in an exhaust train of an internal-combustion engine (10), including:

operating the at least one exhaust-gas sensor at high temperatures at least temporarily and, due to its type of construction, the at least one exhaust-gas sensor is capable of exhibiting a sensitivity to thermal shock, carrying out a heating phase at least temporarily prior to a regeneration phase or prior to a measuring-mode phase, wherein in the heating phase a distinctly lower temperature is adjusted in comparison with a regeneration temperature or a temperature in the measuring-mode phase, adaptively carrying out a dew-point detection and re-enabling of a dew-point end that is influenced by at least one from the group consisting of a fording-detection criterion and a flood-detection criterion, in response to the fording-detection criterion being met and a fording state determined, providing a limiting quantity of heat to be conducted through the at least one exhaust-gas sensor together with exhaust gas to dry the at least one exhaust-gas sensor, and in response to the flooding-detection criterion being met and a flooding state determined, providing a greater quantity of heat to be conducted through the at least one exhaust-gas sensor together with exhaust gas to dry the at least one exhaust-gas sensor as compared to the fording state.

15. The method as claimed in claim 14, wherein the dew-point detection includes temperature quantities of temperature-measuring instruments that have been incorporated within the at least one exhaust-gas sensor or near the at least one exhaust-gas sensor in the exhaust train of the internal-combustion engine (10).

16. The method as claimed in claim 15, including increasing the quantity of heat upon ending of the flooding state or the fording state.

* * * * *